(12) United States Patent
Bei et al.

(10) Patent No.: US 8,323,327 B2
(45) Date of Patent: Dec. 4, 2012

(54) STENT DELIVERY CATHETER SYSTEM AND METHOD OF IMPLANTING A SELF-EXPANDING STENT WITH EMBOLIC PROTECTION

(75) Inventors: Nianjiong Joan Bei, Foster City, CA (US); Keif Fitzgerald, San Jose, CA (US); Patrick C. Saxton, Santa Clara, CA (US); Zhicheng Lin, Palo Alto, CA (US); Steven A. Tyler, Portola Valley, CA (US); Joanna Lubas, Fremont, CA (US)

(73) Assignee: Abbott Cardiovascular Shstems Inc., Santa Clara, CA (US)

( * ) Notice: Subject to any disclaimer, the term of this patent is extended or adjusted under 35 U.S.C. 154(b) by 158 days.

(21) Appl. No.: 12/857,467

(22) Filed: Aug. 16, 2010

(65) Prior Publication Data

US 2010/0331951 A1    Dec. 30, 2010

Related U.S. Application Data

(62) Division of application No. 11/739,743, filed on Apr. 25, 2007, now Pat. No. 7,776,080.

(51) Int. Cl.
*A61F 2/06*    (2006.01)
(52) U.S. Cl. ...... 623/1.11; 623/1.12; 606/108; 606/198; 606/200
(58) Field of Classification Search .................. 606/191, 606/192, 194, 198; 623/1.11–1.12
See application file for complete search history.

(56) References Cited

U.S. PATENT DOCUMENTS

| | | | |
|---|---|---|---|
| 5,019,090 A | 5/1991 | Pinchuk | |
| 5,246,421 A | 9/1993 | Saab | |
| 5,549,635 A | 8/1996 | Solar | |
| 5,634,928 A * | 6/1997 | Fischell et al. | 623/1.11 |
| 5,639,274 A | 6/1997 | Fischell et al. | |
| 5,735,859 A | 4/1998 | Fischell et al. | |
| 5,743,874 A | 4/1998 | Fischell et al. | |
| 5,749,890 A | 5/1998 | Shaknovich | |
| 5,792,144 A | 8/1998 | Fischell et al. | |
| 5,792,157 A | 8/1998 | Mische et al. | |
| 5,980,530 A | 11/1999 | Willard et al. | |
| 6,022,336 A | 2/2000 | Zadno-Azizi et al. | |
| 6,066,158 A | 5/2000 | Engelson et al. | |
| 6,142,987 A * | 11/2000 | Tsugita | 604/500 |
| 6,143,021 A * | 11/2000 | Staehle | 623/1.11 |
| 6,190,393 B1 | 2/2001 | Bevier et al. | |
| 6,398,756 B2 | 6/2002 | Peterson et al. | |
| 6,468,298 B1 | 10/2002 | Pelton | |
| 6,485,500 B1 | 11/2002 | Kokish et al. | |
| 6,485,502 B2 | 11/2002 | Don Michael et al. | |
| 6,582,448 B1 | 6/2003 | Boyle et al. | |
| 6,605,102 B1 | 8/2003 | Mazzocchi et al. | |

(Continued)

*Primary Examiner* — Tuan V Nguyen
(74) *Attorney, Agent, or Firm* — Fulwider Patton LLP

(57) ABSTRACT

A catheter system for implanting an endoprosthesis at a treatment site in a patient's body lumen. The catheter includes an elongated shaft outer member and a stent sheath distal portion and a self-expanding stent radially restrained in a collapsed configuration within the stent sheath distal portion. A balloon catheter dimensioned for relative axial movement within the shaft outer member has an elongated shaft having an inflation lumen and a device receiving lumen. A stent stop secured to the balloon catheter is reversibly radially expandable to deploy from a collapsed to a radially expanded configuration. In the expanded configuration, the stent stop prevents longitudinal displacement of the stent. A balloon is located on a distal shaft section is releasably locked with respect to the shaft outer member and slidably disposed therein in an unlocked configuration.

11 Claims, 6 Drawing Sheets

U.S. PATENT DOCUMENTS

| | | |
|---|---|---|
| 6,629,992 B2 | 10/2003 | Bigus et al. |
| 6,656,213 B2 | 12/2003 | Solem |
| 6,663,651 B2 * | 12/2003 | Krolik et al. .................. 606/200 |
| 6,926,732 B2 * | 8/2005 | Derus et al. .................. 623/1.12 |
| 7,169,165 B2 * | 1/2007 | Belef et al. .................... 606/200 |
| 7,641,684 B2 * | 1/2010 | Hilaire et al. ................. 623/1.35 |
| 7,776,080 B2 * | 8/2010 | Bei et al. ...................... 623/1.11 |
| 2003/0176886 A1 | 9/2003 | Wholey et al. |

* cited by examiner

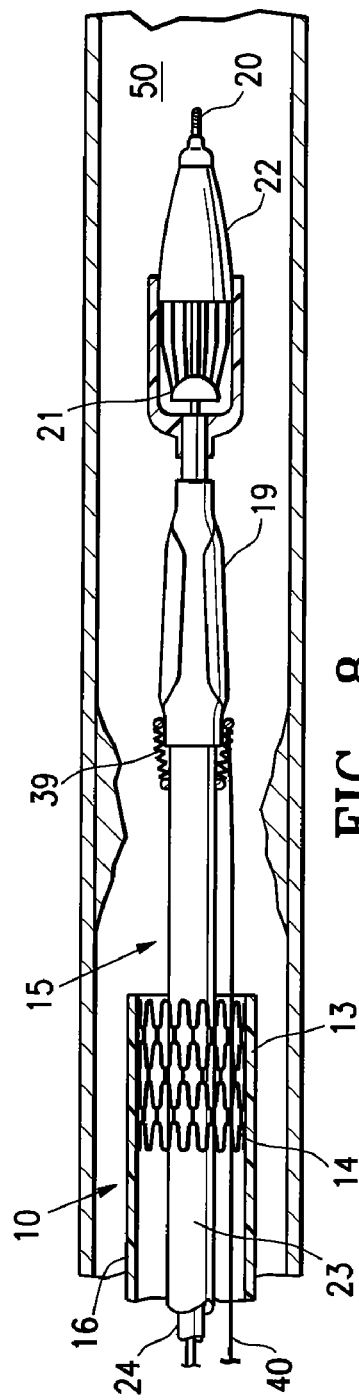
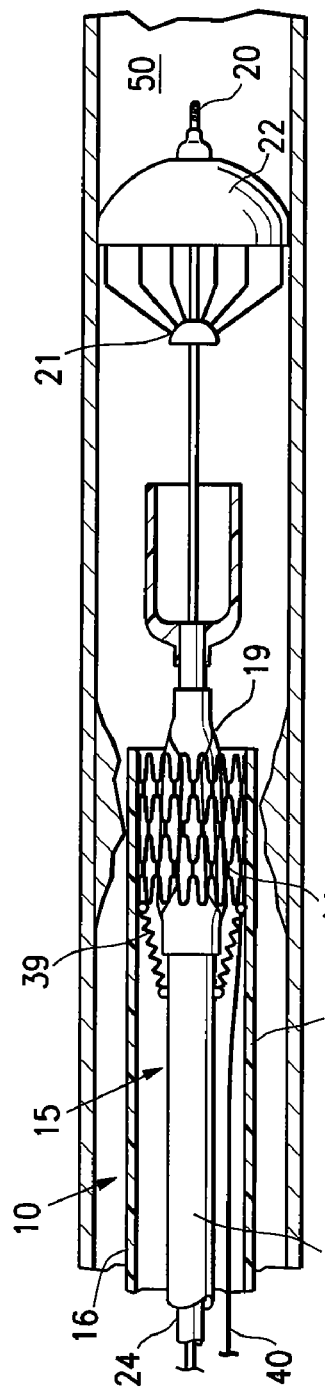
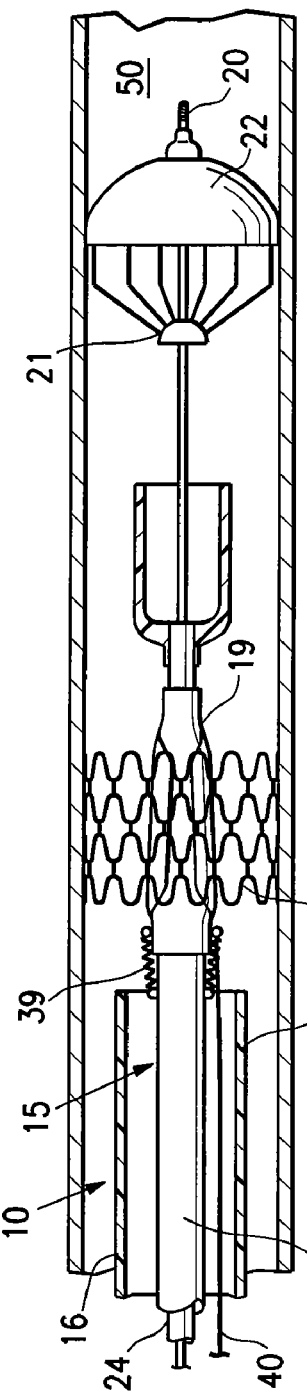
FIG. 8
FIG. 9
FIG. 10

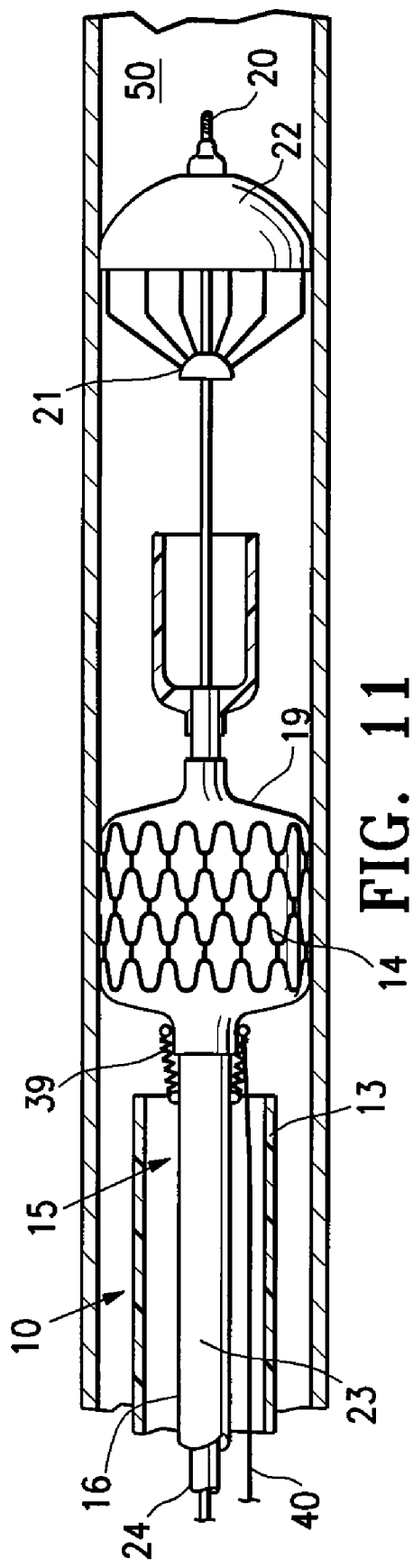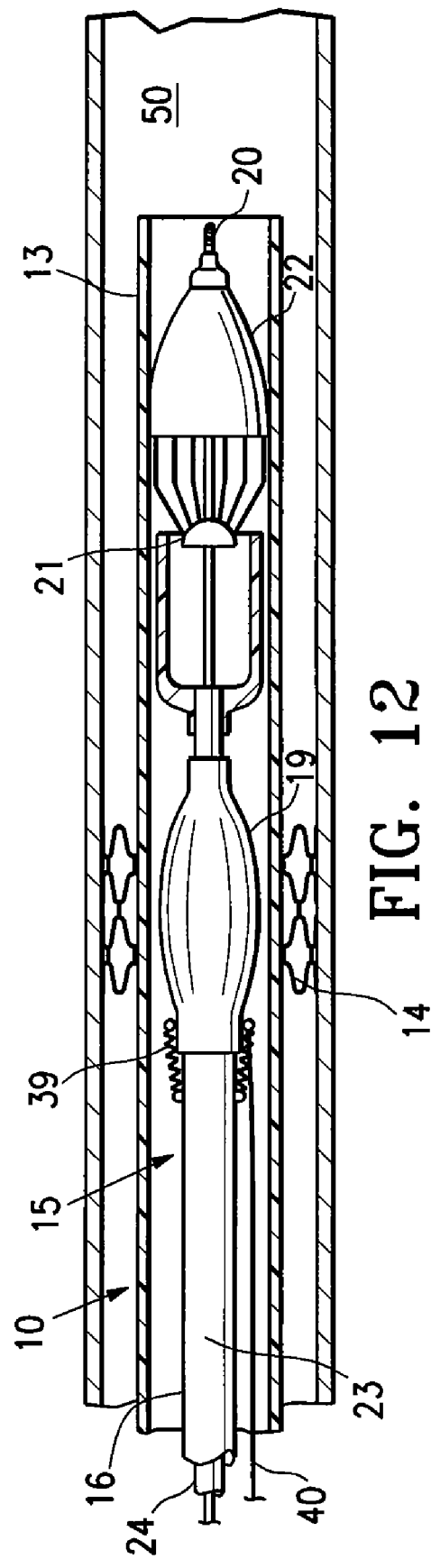

STENT DELIVERY CATHETER SYSTEM AND METHOD OF IMPLANTING A SELF-EXPANDING STENT WITH EMBOLIC PROTECTION

CROSS-REFERENCE TO RELATED APPLICATIONS

This application is a divisional application based on U.S. Ser. No. 11/739,743 filed on Apr. 25, 2007, which issued as U.S. Pat. No. 7,776,080; whose content is hereby incorporated by reference.

BACKGROUND OF THE INVENTION

The present invention relates to interventional catheters, and more particularly to stent delivery systems and methods.

The treatment of an occluded region of a patient's vasculature commonly includes a percutaneous transluminal interventional procedure such as inflating a catheter balloon and/or implanting a stent inside the blood vessel at the site of the stenosis. For example, in balloon angioplasty, the catheter balloon is positioned across the lesion and inflated with fluid one or more times to a predetermined size at relatively high pressures (e.g. greater than 8 atmospheres) so that the stenosis is compressed against the arterial wall and the wall expanded to clear the passageway. Physicians frequently implant a stent inside the blood vessel at the site of the lesion. Stents may also be used to repair vessels having an intimal flap or dissection or to generally strengthen a weakened section of a vessel.

Conventional stents typically fall into two general categories of construction. The first type of stent is expandable upon application of a controlled force, often through the inflation of a catheter balloon or other expansion means on which the stent is mounted, which expands the compressed stent to a larger diameter to be left in place within the artery at the target site. The second type is a self-expanding stent, formed, for example, of shape-memory metals such as super-elastic nickel titanium (NiTi) alloys which will automatically expand from a compressed state when the stent is displaced from the restraining force of the delivery catheter system.

Delivery and deployment of balloon expandable stents at a desired location within the patient's body lumen typically involves advancing a stent delivery balloon catheter through the patient's vascular system until the balloon with the stent mounted thereon is positioned within the treatment area, and then inflating the balloon to expand the stent within the blood vessel. The balloon is then deflated and the catheter withdrawn, leaving the expanded stent within the blood vessel, holding open the passageway thereof. In contrast, implanting self-expanding stents within the patient's vasculature typically involves a method which is different than the one for non-self-expanding stents, and in which the stent expands upon the removal of the force of a radially restraining member. For example, some prior art stent delivery systems for self-expanding stents include a catheter with an inner tubular member upon which the compressed or collapsed stent is mounted, and an outer restraining sheath which is positioned over the compressed stent prior to deployment. When the catheter is in position in the body lumen, the outer sheath is moved in relation to the inner tubular member of the catheter to uncover the compressed stent, allowing the stent to radially self-expand to its expanded condition. Some delivery systems utilize a "push-pull" technique in which the outer sheath is retractable while the inner tubular member is pushed forward or held in place. Still other systems use an actuating wire which is attached to the outer sheath. When the actuating wire is pulled to retract the outer sheath from over the collapsed stent, the inner tubular member must remain stationary, preventing the stent from moving axially within the body vessel. Thus, such self-expanding stents can typically be at least partially expanded without the need for application of a controlled force on the stent, such as is applied through the inflation of the balloon portion of a balloon catheter. However, self-expanding stent delivery systems have been suggested in which inflation of a balloon is required to deploy the self-expanding stent, for example where the balloon is inflated to break or otherwise release the radially restraining member (e.g., outer sheath) from around the collapsed stent.

Implanting the stent may release emboli into the circulatory system, which can be extremely dangerous to the patient. Debris that is carried by the bloodstream to distal vessels of the brain may cause these cerebral vessels to occlude, resulting in a stroke, and in some cases, death. Thus, when performed in a carotid artery, an embolic protection device to capture and collect released emboli may be deployed downstream to the interventional catheter. For example, embolic protection devices in the form of filters or traps can be delivered in a collapsed configuration to a location adjacent to the interventional procedure site, radially expanded to open the mouth of the filter or trap, and after the interventional procedure has been performed, the device is collapsed for removal with the captured embolic material therein.

An essential step in effectively performing an interventional procedure is properly positioning the catheter system at a desired location within the patient's vasculature. The catheter shaft must be able to transmit force along the length of the catheter shaft to allow it to be pushed through the vasculature. However, the catheter shaft must also retain sufficient flexibility and low profile to allow it to track over a guidewire through the often tortuous, narrow vasculature. Such deliverability issues must be balanced against one another and against other performance characteristics. As a result, one design challenge has been making the procedure, including the delivery and retrieval of the components of the catheter system, as quick and easy as possible.

SUMMARY OF THE INVENTION

The invention is directed to a catheter system and method for implanting an endoprosthesis such as a stent at a treatment site in a patient's body lumen. The catheter provides a complete system for stent delivery, dilatation, and recovery of an expanded device, such as an embolic protection device, which is adjacent to the treatment site in the body lumen. In one presently preferred embodiment, the catheter system further provides for embolic protection delivery.

A stent delivery catheter system of the invention generally comprises an elongated shaft outer member with a lumen extending therein and a stent sheath distal portion, a self expanding stent radially restrained in a collapsed configuration within the stent sheath distal portion of the outer member, and a balloon catheter dimensioned for relative axial movement within the shaft outer member. An expandable embolic protection device is constrained by the balloon catheter shaft in the embodiment configured for embolic protection delivery. The balloon catheter has an elongated shaft having an inflation lumen and a device receiving lumen, and a balloon on a distal shaft section having an interior in fluid communication with the inflation lumen such that the balloon is inflatable from a noninflated to an inflated configuration. The balloon catheter is releasably locked with respect to the shaft outer member and slidably disposed therein in an unlocked configuration. The collapsed stent in the stent sheath is coaxially disposed around the noninflated balloon, with an inner surface radially spaced from the outer surface of the noninflated balloon. The collapsed stent is implanted in a patient's body lumen upon release of the radially restraining force of the stent sheath portion of the outer member, which allows the collapsed stent to radially expand from the collapsed configuration to an expanded configuration. To ensure that the stent is fully expanded, the balloon is configured for inflating within the expanded stent, to implant the stent in a fully radially expanded configuration, commonly referred to as a post-dilation or stent-touch up. The catheter system may also be configured for a pre-dilation, in which the balloon is inflated within the stenosis before the stent is radially expanded.

In a presently preferred embodiment, the collapsed stent is not mounted onto a component of the catheter system. Thus, the collapsed stent is free within the stent sheath in a non-mounted configuration, such that the inner surface of the collapsed stent is exposed to and radially spaced from the outer surface of the balloon. The catheter system is configured such that the balloon only contacts the inner surface of the stent upon inflation of the balloon after the stent has radially self-expanded following retraction of the stent sheath.

Following expansion of the stent, the catheter system is configured for recovering a reversibly expanded device such as an embolic protection device which is adjacent to the treatment site in the body lumen. For example, an embolic protection device having a filter on the distal end of a core wire is typically deployed in the patient's body lumen, prior to the stent expansion, in order to filter or otherwise trap any embolic debris released when the stent is subsequently implanted in the body lumen. In a presently preferred embodiment, the stent sheath distal portion of the shaft outer member is configured to be advanced distally through the expanded stent to collapse the operative distal end (i.e., expanded filter) of the embolic protection device therein, so that the embolic protection device can be repositioned or removed from the body lumen. Alternatively, although less preferred, the balloon catheter can have a radially enlarged recovery distal tip configured for collapsing the embolic protection device therein, to thereby recover the embolic protection device within the balloon catheter.

A method of implanting a self-expanding stent in a patient's body lumen with embolic protection generally comprises introducing within a patient's body lumen a self-expanding stent delivery catheter system having a proximal end, a distal end, an elongated shaft outer member with a lumen and a stent sheath distal portion, a self-expanding stent radially restrained in a collapsed configuration within the stent sheath distal portion of the outer member, and a balloon catheter dimensioned for relative axial movement within the shaft outer member. The balloon catheter is releasably locked with respect to the shaft outer member in a locked configuration as the catheter is advanced within the patient's body lumen over a core wire of a device (e.g., an embolic protection device). In the locked configuration, the collapsed stent within the stent sheath is coaxially disposed around the noninflated balloon, such that an inner surface of the stent is radially spaced from the outer surface of the noninflated balloon. At the desired location within the body lumen, the stent sheath is unlocked to allow for proximally retracting the stent sheath from the collapsed stent and noninflated balloon therein, so that the collapsed stent radially spaced from the outer surface of the noninflated balloon radially self-expands at the desired location in the body lumen. In a presently preferred embodiment, the method includes inflating the balloon for pre-dilation before the stent is radially expanded, and/or inflating the balloon within the radially self-expanded stent to implant the stent in a fully radially expanded configuration. The method includes deflating the inflated balloon, and recovering the embolic protection device by advancing the catheter system distally beyond fully radially expanded stent to position the operative distal end of the embolic protection device therein and thereby radially collapse the operative distal end of the embolic protection device. The catheter system can be slidably displaced, with the outer member releasably locked to the balloon catheter and with the collapsed embolic protection device therein, for repositioning or removal from the patient's body lumen.

The catheter system of the invention has flexibility and a low profile despite providing the combined features of self-expanding stent delivery, dilatation, and embolic protection device recovery. Preferably, the catheter system has a profile not greater than current conventional self-expanding stent delivery systems. Thus, the catheter system has a low profile, and has sufficient flexibility to facilitate advancement within the often tortuous anatomy to a desired treatment site in the patient's body lumen.

By advancing the balloon dilatation catheter together with the collapsed self-expanding stent, the system and method of the invention avoids the need to introduce and position a separate balloon catheter for pre-dilating the lesion and/or post-dilating the stent. Similarly, the need for a separate recovery catheter in order to recover the deployed embolic protection device following stent expansion is avoided. These and other advantages of the invention will become more apparent from the following detailed description and accompanying exemplary drawings.

BRIEF DESCRIPTION OF THE DRAWINGS

FIGS. 8-12 illustrate the distal section of a catheter system of the invention in a method of performing a medical procedure in accordance with an embodiment of the invention, with FIG. 8 illustrating the catheter system during delivery of an embolic protection device in a patient's body lumen.

FIG. 9 illustrates the catheter distal portion positioned at a treatment site in a patient's body lumen and proximal to a deployed embolic protection device.

FIG. 10 illustrates the catheter system of FIG. 9 with the stent sheath retracted to allow the stent to radially self-expand.

FIG. 11 illustrates the catheter system of FIG. 10 with the balloon inflated.

FIG. 12 illustrates the balloon catheter system of FIG. 11 with the stent sheath distally advanced to radially collapse the embolic protection device filter therein.

DETAILED DESCRIPTION OF THE PREFERRED EMBODIMENTS

Figure 1:
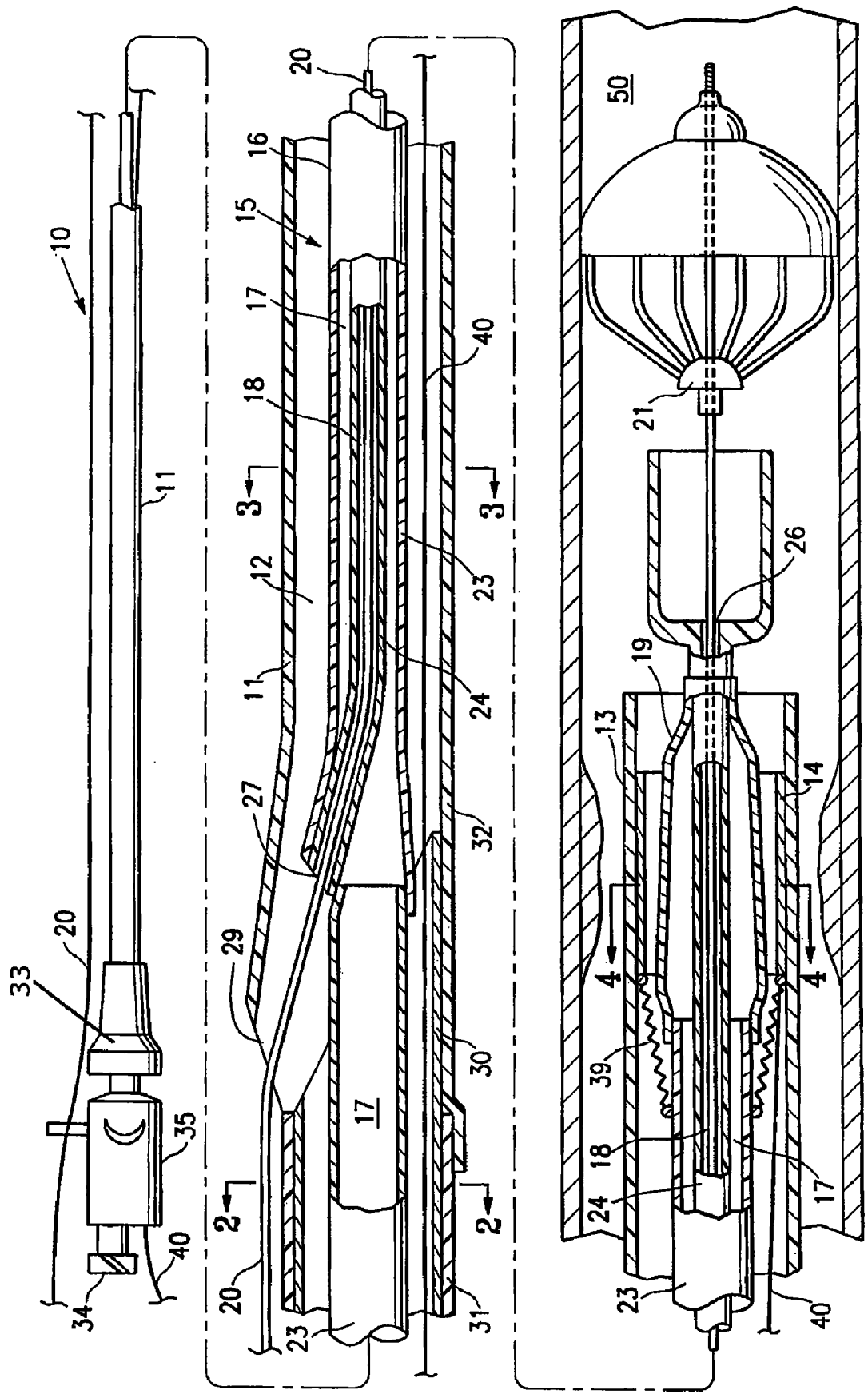
FIG. 1 is an elevational, partially in section, view of a rapid-exchange catheter system embodying features of the invention.

FIG. 1 is an elevational, partially in section, view of a rapid exchange catheter system 10 embodying features of the invention, generally comprising an elongated shaft outer member 11 having a lumen 12 extending therein and a stent sheath distal portion 13, a self-expanding stent 14, and a balloon catheter 15 which is dimensioned for relative axial movement (i.e., longitudinally slidable) within the shaft outer member 11. The self-expanding stent 14 is radially restrained in a collapsed configuration within the stent sheath distal portion 13, and radially expands from the collapsed configuration to an expanded configuration upon release of the radially restraining force of the stent sheath distal portion 13 of the shaft outer member 11. The balloon catheter 15 has an elongated shaft 16 having an inflation lumen 17, and a device receiving lumen 18 configured for slidably receiving a device therein such as the core wire 20 of an embolic protection device 21 or a guidewire (not shown). A balloon 19 on a distal section of the shaft 16 has an interior in fluid communication with the inflation lumen 17 such that the balloon is inflatable from a noninflated to an inflated configuration. The balloon catheter 15 is releasably locked with respect to the shaft outer member 11 and slidably disposed therein in an unlocked configuration.

Figure 4:
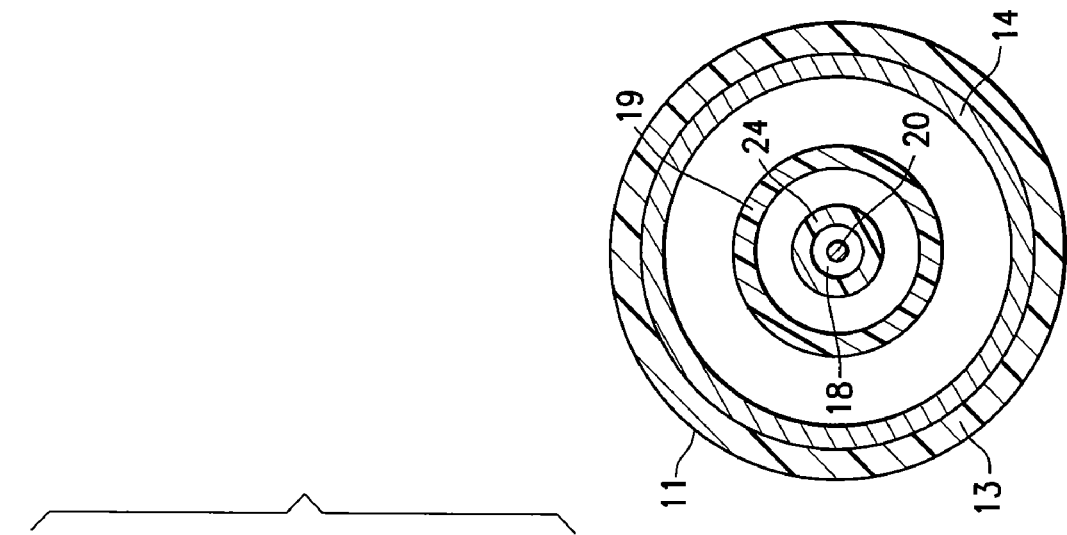
FIGS. 2-4 are transverse cross sections of the catheter system of FIG. 1, taken along lines 2-2, 3-3, and 4-4, respectively.
Figure 2:
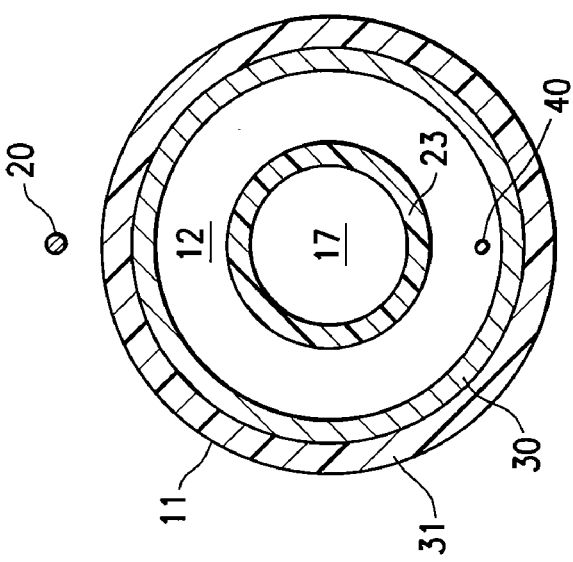
Figure 3:
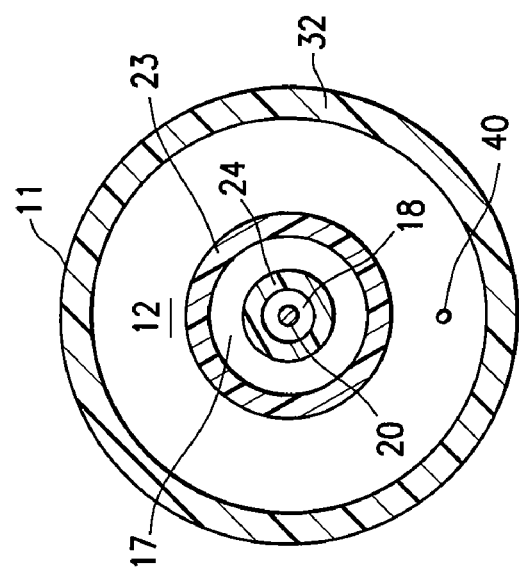

The catheter system 10 is slidably disposed on the core wire 20 of the embolic protection device 21, and in the embodiment of FIG. 1 is configured to advance the contained embolic protection device 21 to a desired location in the patient's body lumen 50 with the balloon in the low-profile noninflated configuration and the stent collapsed within the shaft outer member 11. The catheter system can alternatively be slidably advanced over the core wire 20 of a previously delivered embolic protection device 21. At the desired location, the catheter system 10 allows for deploying the embolic protection device, pre-dilating the lesion, implanting the stent 14, and then recovering the embolic protection device 21 by radially collapsing the operative distal end thereof within a lumen of the catheter system 10, as discussed in more detail below. FIG. 1 illustrates the balloon 19 in the noninflated configuration and the stent 14 in the collapsed configuration within the stent sheath distal portion 13 of the shaft outer member 11, after the catheter system 10 has been advanced to the desired treatment location in the body lumen 50, located proximally adjacent to the deployed operative distal end of the embolic protection device 21. FIGS. 2-4 illustrate transverse cross sections of the catheter of FIG. 1, taken along lines 2-2, 3-3, and 4-4, respectively. For ease of illustration, the noninflated balloon 19 is shown radially spaced from the outer surface of the section of the shaft 16 extending within the inflatable interior of the balloon 19, although it should be understood that the noninflated balloon is typically collapsed onto the shaft 16 to a low profile configuration for advancement within the patient's body lumen 50.

The stent sheath portion 13 of the outer member 11 is configured to releasably retain the stent in a radially collapsed configuration for delivery within the body lumen 50. The outer member 11 can have a uniform composition and diameter along the entire length of the outer member 11 (including along the stent sheath distal portion 13), or alternatively a variable composition and/or diameter along its length. The collapsed stent 14 in the stent sheath portion 13 of the shaft outer member 11 is coaxially disposed around the noninflated balloon 19 and has an inner surface radially spaced from the outer surface of the noninflated balloon 19. Thus, the collapsed stent 14 is free within the stent sheath portion 13 of the shaft outer member 11 in a non-mounted configuration such that the inner surface of the collapsed stent 14 is exposed to and radially spaced from the outer surface of the balloon 19 and remaining components of the catheter system 10 extending through the collapsed stent 14.

In the illustrated embodiment, the balloon catheter shaft 16 comprises an outer tubular member 23 having the inflation lumen 17 therein and an inner tubular member 24 having the device receiving lumen 18 therein, although a variety of suitable shaft configurations can be used as are conventionally known. The device receiving lumen 18 of the balloon catheter 15 extends from a distal port 26 at the distal end of the balloon catheter 15 to a proximal port 27. The balloon catheter 15 has a radially enlarged delivery distal tip configured to releasably retain the operative distal end of the embolic protection device 21 in a collapsed configuration therein for delivery within the body lumen 50. In the embodiment illustrated in FIG. 1, the balloon catheter 15 is a rapid-exchange type catheter, so that the device receiving lumen 18 of the balloon catheter 15 extends within the balloon catheter distal shaft section to the proximal port 27 distally spaced from a proximal end of the balloon catheter shaft 16. In an alternative embodiment illustrated in FIG. 5, the balloon catheter 15 is an over-the-wire type catheter, so that the device receiving lumen 18 extends to the proximal end of the balloon catheter shaft 16. Specifically, in the catheter system 10' of FIG. 5, the inner tubular member 24 proximal port 27 (not shown in FIG. 5) is at the proximal end of the shaft 16. In the catheter system 10' of FIG. 5, the shaft outer member 11 has rapid-exchange proximal port 29 similar to the embodiment of FIG. 1. Alternatively, FIG. 7 illustrates an over-the-wire catheter system 10" embodying features of the invention, as discussed in more detail below.

Figures 5, 6:
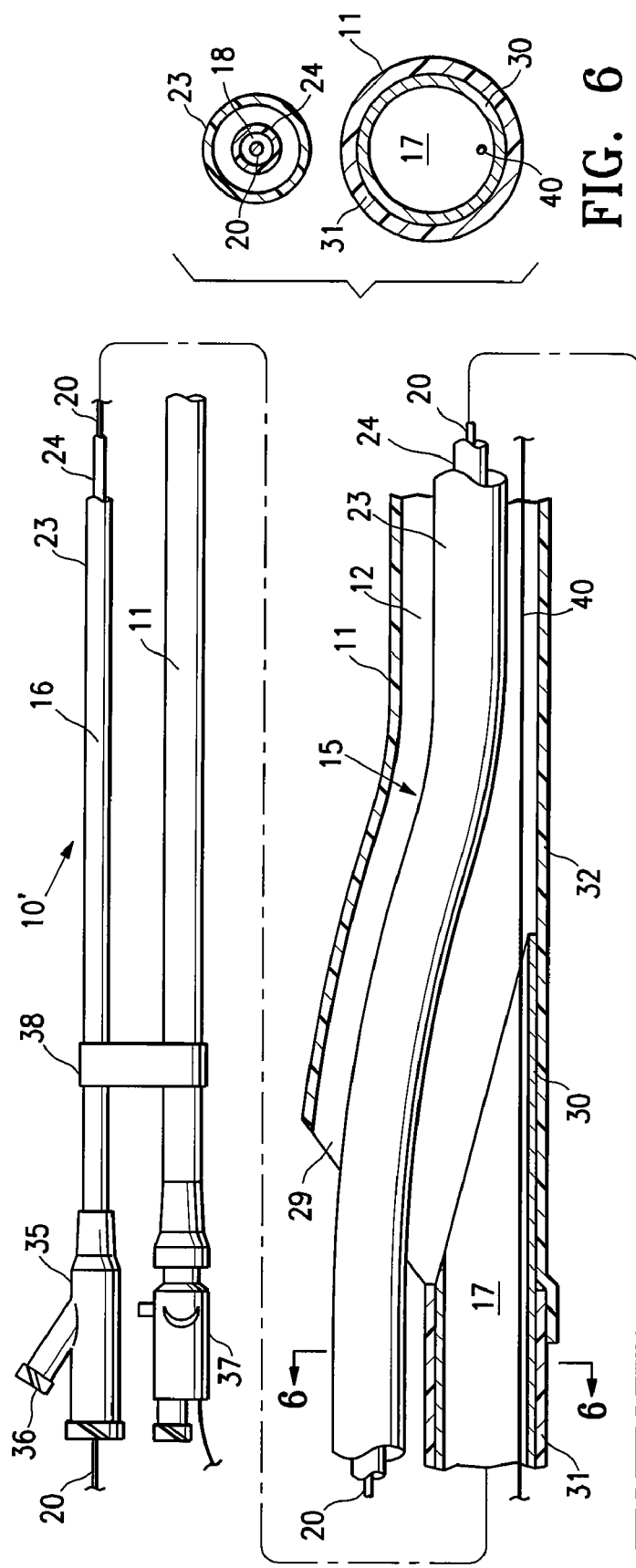
FIG. 5 is an elevational, partially in section, view of an alternative embodiment of the catheter system, in which the balloon catheter is an over-the-wire catheter.
FIG. 6 is a transverse cross section of the catheter of FIG. 5, taken along line 6-6.
Figure 7:
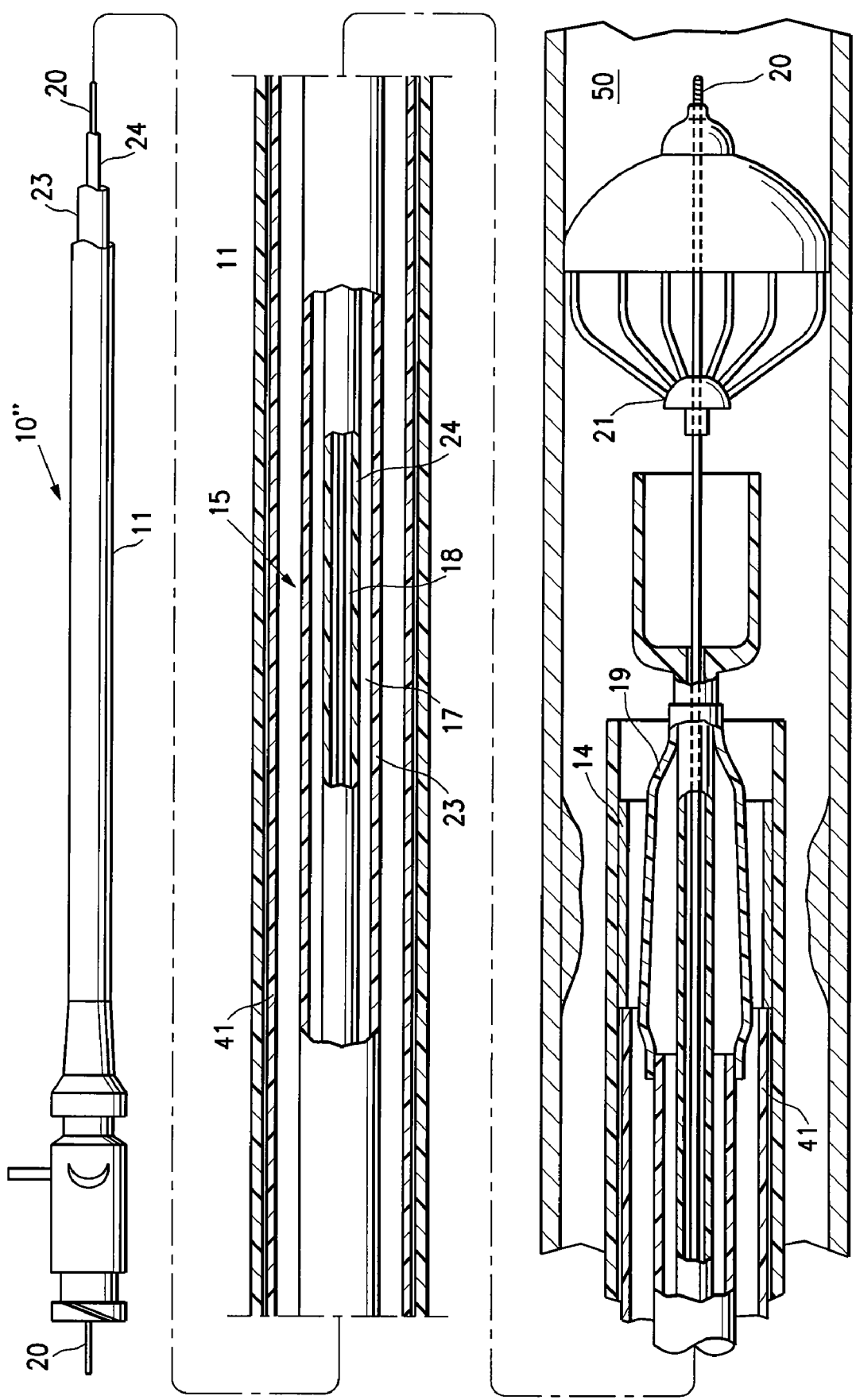
FIG. 7 is an elevational, partially in section, view of an over-the-wire catheter system embodying features of the invention.

The shaft outer member 11 has a distal port 28 at the distal end of the outer member, a proximal port (not shown) at the proximal end of the outer member, and a rapid-exchange proximal port 29 distally spaced from the proximal end of the outer member which is configured to slidably receive a device therethrough such as the core wire 20 of the embolic protection device 21 as illustrated in the embodiment of FIG. 1, or the balloon catheter shaft 16 and core wire 20 as illustrated in the embodiment of FIG. 5. In the illustrated embodiments, the shaft outer member 11 comprises a tubular member 30 which form a proximal section of the outer member 11, and a polymeric tubular member 32 which forms a distal section of the outer member 11. Tubular member 30 is typically formed of a relatively high strength material providing axial support for force transmission (pushability), with single or multiple lumens therein. A polymeric outer layer 31 is provided on the axial supporting tubular member 30. The tubular member 30 is typically a metallic tube, although a variety of high strength members can alternatively be used including high strength or reinforced polymeric members such as a coil, or braided material. Additionally, depending upon the support provided by the balloon catheter shaft 16, the high strength (stiff) tubular member 30 of the shaft outer member 11 may be omitted, as for example, in an embodiment in which the balloon catheter shaft 16 has a high strength tube (e.g., hypotube) proximal shaft section.

A proximal adapter 33 on the proximal end of the shaft outer member 11 and balloon catheter shaft 16, has a port 34 configured for connecting to a source of inflation fluid (not shown) for inflating the balloon 19. In the embodiment illustrated in FIG. 1, the proximal adapter 33 functions as a handle having a mechanism which can be activated to move the shaft outer member 11 relative to the balloon catheter shaft 16 therein. The proximal adapter handle 33 also typically has a lock mechanism to releasably secure the shaft outer member 11 to the balloon catheter shaft 16. Such handle mechanisms are generally known and typically include a thumb wheel, trigger, lever or other activation mechanism for advancing and/or retracting a shaft. A variety of suitable mechanisms may be used to clamp or otherwise releasably lock the shaft outer member 11 to the balloon catheter shaft 16 as are conventionally known, typically in the form of a clamp or other locking mechanism at or near the proximal end of the shaft outer member 11. The proximal adapter handle 33, operatively connected to both the shaft outer member 11 and balloon catheter shaft 16, preferably constrains the rotation of the balloon catheter 15 within the outer member 11 to thereby hold the proximal port 27 of the balloon catheter device receiving lumen 18 rotationally aligned with the outer member rapid-exchange proximal port 29. As a result, extending the core wire 20 of the embolic protection device 21 through the rotationally aligned ports 27 and 29 is facilitated, so that the core wire 20 extends along the exterior of the proximal section of the outer member 11. In the embodiment of FIG. 5, the shaft outer member 11 and balloon catheter 15 do not meet at a common proximal adapter handle. Rather, the balloon catheter has a proximal adapter 35 on the proximal end of the balloon catheter shaft 16 with a port 36 configured for connecting to a source of inflation fluid (not shown) for inflating the balloon 19, and a proximal adapter handle 37, similar to handle 33 of FIG. 1, is on the proximal end of the shaft outer member 11. In the embodiment of FIG. 5, a collar 38 on the proximal shaft sections of the shaft outer member 11 and balloon catheter shaft 16 is configured to releasably hold the shaft outer member 11 and balloon catheter shaft 16 together.

Activation of the mechanism of the handle 33 causes the shaft outer member 11 to be proximally retracted from its FIG. 1 position relative to the stent 14 and balloon catheter 15 therein, to thereby radially self-expand the stent 14 in the body lumen 50. In the retracted position, the distal end of the shaft outer member 11 is typically located proximally adjacent to the proximal end of the balloon. During retraction of the shaft outer member, a stent stop 39 is configured to prevent longitudinal displacement of the stent 14 within the outer member 11 proximally of the stent stop 39. A variety of suitable designs can be used including stent stops which are permanently mounted to the balloon catheter shaft and which may or may not be deployable. In embodiments illustrated in FIGS. 1 and 5, stent stop 39 is a deployable (i.e., reversibly radially collapsible) cone shaped member fixedly secured to the balloon catheter shaft at a location proximally adjacent to the proximal end of the balloon. An activation wire 40 secured to the distal end of the stent stop 39 can be used to reversibly radially expand/collapse the stent stop 40. In FIGS. 1 and 5, the stent stop 39 is illustrated in the expanded configuration which prevents proximal movement of the collapsed stent 14 during proximal retraction of the shaft outer member 11 from around the stent 14 to implant the stent 14 in the body lumen 50. In the radially collapsed configuration (see e.g., FIG. 8) the deployable stent stop 39 is radially collapsed sufficiently to allow the balloon catheter 15 to be slidably advanced distally of the collapsed stent 14, in order to deploy the embolic protection device 21 and/or predilate the lesion prior to radial expansion of the stent 14. Alternatively, a stent stop which is not fixedly mounted onto the balloon catheter can be used. For example, a stent stop comprising a separate concentric sheath outside of the balloon catheter 15 and inside of the shaft outer member 11 allows for movement of the balloon catheter 15 distally from the collapsed stent 14 without requiring radial deployment of the stent stop, as discussed in more detail below regarding the embodiment of FIG. 7.

FIG. 7 is an elevational, partially in section, view of an over-the-wire catheter system 10" embodying features of the invention, with similar components having the same reference numerals as in the embodiment of FIG. 1. In the over-the-wire catheter system 10" both the shaft outer member 11 and the balloon catheter 15 are over-the-wire-type catheters, i.e., without rapid-exchange proximal ports 27 and 29 distally spaced from the proximal ends thereof. The over-the-wire catheter system 10" of the embodiment of FIG. 7 has a stent stop 41 comprising a separate concentric sheath outside of the balloon catheter 15 and inside of the shaft outer member 11. Unlike the radially deployable stent stop 39 of the embodiment of FIG. 1, the stent stop 41 is a tube which not reversibly collapsible. However, the stent stop 41 is not fixedly secured to the balloon catheter 15 and therefore allows for movement of the balloon catheter 15 distally from the collapsed stent 14 for embolic protection delivery and/or predilation. Similar to the rapid exchange embodiment, the catheter system 10" is configured for slidably advancing, with the core wire 20 of the embolic protection device 21 therein, to a desired location in the patient's body lumen 50 with the balloon in the low-profile noninflated configuration and the stent collapsed within the shaft outer member 11.

FIGS. 8-12 illustrate the balloon catheter system 10, partially in section, during a method of performing a procedure in accordance with an embodiment of the invention, in which the self-expanding stent 14 is implanted in the patient's body lumen 50 and then the catheter system 10 is used to recover the radially expanded embolic protection device 21 previously deployed in the body lumen 50. Specifically, the catheter system 10 is advanced within the body lumen 50 to implant the stent 14 therein at a treatment site located proximal to the distal end of the deployed embolic protection device 21. The embolic protection device 21 is preferably delivered using the catheter system 10 of the invention. The catheter system of the invention is configured to allow for embolic protection delivery and/or predilation in the embodiments which have a deployable stent stop or a concentric sheath stent stop. In contrast, embodiments which have a nondeployable stent stop fixedly secured within the shaft outer member (e.g., fixedly secured to the balloon catheter 15) do not allow for the balloon catheter to be advanced distally from the collapsed stent and thus are not configured for embolic protection delivery or for predilation. Therefore, in alternative embodiments, the embolic protection device 21 is delivered and deployed in the body lumen 50 using a delivery catheter (not shown) which is then removed prior to positioning of the balloon catheter system of the invention. Details regarding embolic protection devices and delivery systems can be found in U.S. Pat. No. 6,695,813 incorporated by reference herein in its entirety.

FIG. 8 illustrates the system 10 advanced in the body lumen 50 and into position for delivery of the embolic protection device 21. Specifically, the catheter system 10 is advanced with the embolic protection device collapsed within the distal delivery tip of the balloon catheter 15. Preferably, the system 10 is introduced and advanced within the body lumen 50 with the shaft outer member 11 releasably locked to the balloon catheter 15, and with the stent stop 39 in a collapsed configuration. Once at the desired treatment site, the method includes unlocking and distally advancing the balloon catheter 15 from the shaft outer member 11 and collapsed stent 14 to position the distal end of the balloon catheter distal to the stent implantation site as illustrated in FIG. 8. The balloon catheter 15 is then proximally retracted from the embolic protection device 21 to thereby radially expand the operative distal end of the embolic protection device 21 in the body lumen 50. The illustrated embolic protection device 21 is of the type having a self-expanding filter 22 which is on a distal section of the elongated core wire 20, and FIG. 9 illustrates the device 21 with the filter 22 radially expanded into contact with the vessel wall inner surface such that the filter 22 will trap embolic material in the body lumen 50.

With the balloon 19 spaced distally from the shaft outer member 11, the balloon can be inflated in a predilation procedure which dilates the lesion prior to implanting the stent 14. Preferably, the balloon material is highly elastic such that the balloon deflates to a low profile following the predilation to facilitate positioning the collapsed stent within the predilated lesion around the deflated balloon. Alternatively, if the deflated balloon profile is significantly bigger than the original balloon profile (not highly elastic) the balloon cannot perform the predilation function or the deflated balloon must be advanced distal to the lesion following predilation to allow for stent deployment.

Following embolic protection delivery and optional predilation of the lesion, the shaft outer member 11 with the collapsed stent 14 therein is advanced into position for stent implantation at the lesion. Once at the desired treatment site, the stent stop 39 is deployed using activation wire 40, to a radially expanded diameter equal to a diameter of the collapsed stent 14 as illustrated in FIG. 9. A variety of suitable mechanisms can be used to deploy the stent stop 39 which may be biased to the deployed or the collapsed configuration. In a presently preferred embodiment, the stent stop 39 has a biased (i.e., relaxed) radially collapsed configuration. With the stent stop 39 radially expanded at the proximal end of the collapsed stent, the method includes unlocking and proximally retracting the outer member 11 from the collapsed stent 14 and noninflated balloon 19 therein, so that the collapsed stent 14 radially expands at a location in the body lumen proximal to the operative distal end (e.g., filter 22) of the embolic protection device 21. FIG. 10 illustrates the shaft outer member 11 in the fully retracted configuration and the stent 14 in the radially self-expanded configuration in the body lumen 50. After the stent self-expands, the deployable stent stop 39 is preferably radially collapsed to the collapsed configuration (see FIG. 11).

The method typically includes inflating the balloon within the self-expanded stent, commonly referred to as a post-dilatation/stent touch-up, to thereby implant the stent 14 in a fully radially expanded configuration. FIG. 11 illustrates the balloon 19 inflated within the stent 14 in order to radially expand the stent 14 to the fully expanded configuration to thereby implant the stent 14 in the body lumen 50, with the embolic protection device 21 remaining deployed distal to the stent 14 to capture any embolic material released during the procedure. The balloon 19, configured for radially expanding stent 14, typically has a relatively high working pressure (for example, a nominal pressure of about 6 to about 12 atm), and a relatively high wall strength, to expand the stent 14 without rupturing.

After the stent touch-up, the balloon 19 is deflated, and the method includes recovering the embolic protection device 21 by advancing the catheter system 10 distally beyond implanted stent 14 to position the operative distal end 22 of the embolic protection device 21 therein and thereby radially collapse the operative distal end 22 of the embolic protection device 21. In the embodiment illustrated in FIG. 12, recovering the embolic protection device 21 comprises advancing the shaft outer member 11 distally to an advanced position to collapse the operative distal end 22 of the device 21 within the stent sheath portion 13 of the outer member 11. Typically, the shaft outer member 11 is advanced distally over the deflated balloon 19 and then locked with respect to the balloon catheter 15 before being distally advanced further to collapse the operative distal end 22 of the device 21 within the stent sheath 13. The stent sheath distal portion 13 thus typically has an inner diameter dimensioned to be slidably advanceable distally past the deflated balloon 19. However, the embolic protection device 21 can be recovered within an alternative component of the catheter system 10. For example, although less preferred, recovering the embolic protection device can alternatively comprise advancing the balloon catheter 15 distally to collapse the operative distal end 22 of the device 21 within a radially enlarged recovery distal tip of the balloon catheter elongated shaft 16. A radially enlarged recovery distal tip would typically be similar to the radially enlarged delivery distal tip of the embodiment of FIG. 1, although generally with a larger diameter to facilitate receiving the expanded operative distal end 22 of the embolic protection device 21 (which may have embolic debris therein).

Following recovery of the embolic protection devise 21 within the catheter system 10, the catheter system 10 can be repositioned or removed from the patient's body lumen 50, Preferably with the shaft outer member releasably locked to the balloon catheter 15.

The catheter system components can be formed by conventional techniques, for example by extruding materials already found useful in intravascular catheters such a polyethylene, polyvinyl chloride, polyesters, polyamides, polyimides, polyurethanes, and composite materials. The various components may be joined using conventional bonding methods such as by fusion or adhesive bonding. A variety of suitable self-expanding stents as are conventionally known can be used with the catheter system of the invention, and details regarding self-expanding stents can be found in U.S. Pat. No. 6,375,676, incorporated by reference herein in its entirety.

While the present invention is described herein in terms of certain preferred embodiments, those skilled in the art will recognize that various modifications and improvements may be made to the invention without departing from the scope thereof. For example, although discussed primarily in terms of recovery of an embolic protection filter having a frame of spaced apart, longitudinal struts, alternative reversibly expandable devices can be recovered using a catheter system of the invention, including embolic protection devices not having this frame-type construction. Thus, the catheter system 10 of the invention can be configured for recovering a variety of deployed devices, which are recovered by radially collapsing from an expanded configuration, and which are configured for a variety of purposes including, for example, drug or fluid delivery, and temporary support of the body lumen. Additionally, although the balloon catheter shaft 16 is illustrated as having an inner and outer tubular member 24, 23, a variety of suitable shaft configurations may be used including a dual lumen extruded shaft having a side-by-side lumens extruded therein. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments of the invention.

We claimed:

1. A stent delivery catheter system, comprising:
   a) an elongated shaft outer member having a lumen extending therein and a stent sheath distal portion, and a self-expanding stent which is radially restrained in a collapsed configuration within the stent sheath distal portion and which radially expands from the collapsed configuration to an expanded configuration upon release of the radially restraining force of the stent sheath distal portion of the shaft outer member; and b) a balloon catheter dimensioned for relative axial movement within the shaft outer member, which has an elongated shaft having an inflation lumen and a device receiving lumen, a stent stop fixedly secured to the balloon catheter which is reversibly radially expandable to deploy from a collapsed to a radially expanded configuration, wherein in the expanded configuration the stent stop being configured to prevent longitudinal displacement of the stent within the shaft outer member proximally of the stent stop, and a balloon on a distal section of the elongated shaft having an interior in fluid communication with the inflation lumen such that the balloon is inflatable from a noninflated to an inflated configuration, and which is releasably locked with respect to the shaft outer member and slidably disposed therein in an unlocked configuration, wherein the collapsed stent in the stent sheath distal portion is coaxially disposed around the noninflated balloon and has an inner surface radially spaced from an outer surface of the noninflated balloon.

2. The catheter system of claim 1 wherein the collapsed stent is free within the stent sheath distal portion in a non-mounted configuration such that the inner surface of the collapsed stent is exposed to and radially spaced from the outer surface of the balloon.

3. The catheter system of claim 1 wherein the balloon catheter has a radially enlarged delivery distal tip configured to releasably contain at least a portion of an expandable embolic protection device in a collapsed configuration therein.

4. The catheter system of claim 1 wherein the stent sheath distal portion has an inner diameter dimensioned to be slidably advanceable distally past the deflated balloon.

5. The catheter system of claim 1 wherein the balloon catheter has a radially enlarged recovery distal tip configured to slidably receive at least a portion of an expanded embolic protection device to collapse and thereby recover the device therein.

6. The catheter system of claim 1 wherein the shaft outer member has a distal port at the distal section thereof, and a rapid-exchange proximal port distally spaced from a proximal end of the shaft outer member, which are configured to slidably receive a device therein.

7. The catheter system of claim 6 wherein the balloon catheter is a rapid-exchange catheter, so that the device receiving lumen of the balloon catheter extends from a distal port at the distal section of the elongated shaft to a proximal port distally spaced from a proximal end of the elongated shaft and is configured to slidably receive a wire therein, and the balloon catheter extends within a proximal and a distal section of the shaft outer member to the proximal end of the shaft outer member.

8. The catheter system of claim 7 wherein a proximal adapter handle on the proximal end of the shaft outer member releasably locks the balloon catheter to the shaft outer member.

9. The catheter system of claim 6 wherein the balloon catheter is an over-the-wire catheter, so that the device receiving lumen of the balloon catheter extends from a distal port at the distal section of the elongated shaft to a proximal port at a proximal end of the elongated shaft, and the balloon catheter extends within a distal section of the shaft outer member, and extends exterior to a proximal section of the shaft outer member located proximal to the rapid-exchange proximal port of the shaft outer member.

10. The catheter system of claim 1 wherein the shaft outer member and the balloon catheter are both over-the-wire catheters, so that the device receiving lumen of the balloon catheter extends from a distal port at the distal section of the elongated shaft to a proximal port at a proximal end of the elongated shaft, and the balloon catheter extends within a proximal and a distal section of the shaft outer member to the proximal end of the shaft outer member.

11. A stent delivery catheter system, comprising:
a) an elongated shaft outer member having a lumen extending therein and a stent sheath distal portion;
b) a self-expanding stent restrained in a collapsed configuration within the stent sheath distal portion and which radially expands from the collapsed configuration to an expanded configuration upon retraction of the stent sheath distal portion; and
c) a balloon catheter dimensioned for relative axial movement within the shaft outer member, which has an elongated shaft having an inflation lumen, a balloon on a distal section of the elongated shaft in fluid communication with the inflation lumen such that the balloon is inflatable from a noninflated to an inflated configuration, the balloon catheter being releasably locked with respect to the shaft outer member and slidably disposed therein in an unlocked configuration, and a stent stop fixedly secured to the elongated shaft of the balloon catheter which is expandable between a collapsed configuration and an expanded configuration, wherein in the expanded configuration the stent stop being configured to prevent longitudinal displacement of the stent within the shaft outer member proximally of the stent stop.

* * * * *